United States Patent [19]

Helsley et al.

[11] Patent Number: 5,192,776
[45] Date of Patent: Mar. 9, 1993

[54] 1-SUBSITUTED-4-PENTAFLUOROPHENOX-YPIPERIDINES

[75] Inventors: Grover C. Helsley, Pluckemin; Larry Davis, Sergeantsville; Gordon E. Olsen, Somerset, all of N.J.

[73] Assignee: Hoechst-Roussel Pharmaceuticals Incorporated, Somerville, N.J.

[21] Appl. No.: 764,280

[22] Filed: Sep. 23, 1991

Related U.S. Application Data

[63] Continuation of Ser. No. 167,935, Mar. 14, 1988, abandoned.

[51] Int. Cl.$^5$ .................. A61K 31/445; C07D 211/46
[52] U.S. Cl. .................................. 514/327; 546/221; 546/194; 546/210; 546/209; 546/199; 514/318; 514/322; 514/326
[58] Field of Search ..................... 546/221; 514/327

[56] References Cited

U.S. PATENT DOCUMENTS

| | | | |
|---|---|---|---|
| 4,518,713 | 5/1985 | Kosley et al. | 514/326 |
| 4,529,730 | 7/1985 | Schneider et al. | 514/321 |
| 4,547,514 | 10/1985 | Mathur et al. | 514/327 |

FOREIGN PATENT DOCUMENTS 1280699  7/1972  United Kingdom .

OTHER PUBLICATIONS

Boswell, et al., *J. Med. Chem.*, "Synthesis of Some N-Carboxylic Acid Derivatives of 3-Phenoxypiperidines . . ." 17(9) pp. 1000–1008 (1974).

*Primary Examiner*—Carolyn Elmore
*Assistant Examiner*—Mark W. Russell
*Attorney, Agent, or Firm*—Elliott Korsen

[57] ABSTRACT

Carbonyl derivatives of 4-pentafluorophenoxypiperidines and methods for treating convulsions, depression, and hypertension utilizing compounds or compositions thereof are disclosed.

13 Claims, No Drawings

1-SUBSTITUTED-4-PENTAFLUOROPHENOX-YPIPERIDINES

This is a continuation, of application Ser. No. 167,935 filed Mar. 14, 1988 now abandoned.

This invention relates to 1-carbonyl derivatives of 4-pentafluorophenoxypiperidines. More particularly, this invention relates to 1-substituted-4-pentafluorophenoxypiperidines of the formula:

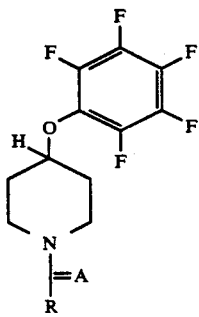

FORMULA I wherein A is oxygen or sulfur, and R is hydrogen, loweralkyl, arylloweralkyl, heteroarylloweralkyl, amino, loweralkylamino, diloweralkylamino, or arylamino; which compounds, alone or in combination with one or more pharmaceutically acceptable carriers, are useful for treating depression, treating convulsions, and reducing blood pressure.

Throughout the specification and appended claims a given formula or name shall encompass the stereo, optical, and geometrical isomers thereof, as well as the pharmaceutically acceptable acid addition salts and solvates (e.g., hydrates) of same.

Subgeneric to the N-substituted-4-pentafluorophenoxypiperidines of this invention are Formula I compounds wherein
(a) A is oxygen;
(b) A is sulfur;
(c) R is hydrogen;
(d) R is loweralkyl;
(e) R is amino;
(f) R is loweralkylamino;
(g) R is diloweralkylamino;
(h) R is arylamino;
(i) R is arylloweralkyl; and
(j) R is heterarylloweralkyl.

As used throughout the specification and appended claims the term "loweralkyl" shall mean a linear or branched, acyclic hydrocarbon radical containing no unsaturation and having the formula $—C_xH_{2x+1}$ wherein x is an integer having a value of 1 to 7, inclusive, such as methyl, ethyl, 1-propyl, 2-propyl, 1-butyl, 1-pentyl, 2-pentyl, 3-hexyl, 4-heptyl, and the like; the term "loweralkoxy" shall mean an acyclic organic racical of the formula $—OC_xH_{2x+1}$ wherein x is an integer having a value of 1 to 7, inclusive, such as methoxy, ethoxy, 1- and 2-propoxy, 1,2-dimethylethoxy, 1-butoxy, 1- and 2-pentoxy, 3-hexoxy, 4-heptoxy and the like; the term "halogen" shall mean a member of the group consisting of fluorine, chlorine, bromine, and iodine radicals; the term "aryl" shall mean a phenyl group optionally substituted by one or more substitutents selected from the group consisting of halogen, loweralkyl, loweralkoxy, and trifluoromethyl; the term "arylloweralkyl" shall mean a loweralkyl group having an substituent thereon; the term "heteroary" shall mean an aromatic heterocyclic mono- or dicyclic radical such as, for example, pyridyl, pyrazinyl, quinolinyl, benzimidazolyl, thienyl, thiazolyl, imidazolyl, benzisoxazolyl, and the like, optionally substituted by one or more substitutents selected from the group consisting of halogen, loweralkyl, and loweralkoxy; the term "heteroarylloweralkyl" shall mean a loweralkyl group having a heteroaryl substituent thereon; the term "amino" shall mean a group of the formula $—NH_2$; the term "loweralkylamino" shall mean an amino group substituted at the nitrogen atom thereof by a loweralkyl group; and the term "arylamino" shall mean an amino group substituted at the nitrogen atom thereof by an aryl group.

The 1-substituted-4-pentafluorophenoxypiperidines of this invention are synthesized by the processes illustrated in the Reaction Scheme which follows.

As illustrated, 1-benzyl-4-hydroxypiperidine 1a is reacted with pentafluorophenol 2a to produce 1-benzyl-4-(2,3,4,5,6-pentafluorophenoxy)piperidine 3a which in turn is converted to 4-(2,3,4,5,6-pentafluorophenoxy)-piperidine 4a from which a variety of 1-carbonyl derivatives 5a may be produced.

The reaction of 1-benzyl-4-hydroxypiperidine 1a with pentafluorophenol 2a is conducted in the presence of triphenylphosphine and diethylazodicarboxylate. Desirably, triphenylphosphine and diethylazodicarboxylate are utilized in quantities slightly in excess of stoichiometric amounts; the use of about a 10% excess of triphenylphosphine and diethylazodicarboxylate being preferred. The reaction is generally conducted in a non-reactive organic solvent at a temperature of from about 5° C. to about 50° C., preferably from about 10° C. to about 30° C. Suitable solvents include aromatic hydrocarbons as previously described; benzene being preferred.

Removal of the benzyl protecting group of the 1-benzyl-4-(2,3,4,5,6-pentafluorophenoxy)piperidine 3a to afford the 4-(2,3,4,5,6-pentafluorophenoxy)piperidine 4a is generally achieved by catalytic reduction. Reaction with hydrogen in the presence of an appropriate catalyst (e.g. palladium, platinum, and the like; 10% palladium on carbon being preferred) at a pressure of from about 30 psi to about 50 psi, preferably from about 45 psi to about 55 psi, and a temperature of from about 10° C. to about 50° C., preferably from about 20° C. to about 30° C., is suggested as a convenient means of deprotection.

Substitution at the nitrogen atom of the 4-(2,3,4,5,6-pentafluorophenoxy)piperidine 4a may be accomplished by any of numerous methods known in the art. For example, Formula I compounds wherein R is loweralkylamino or arylamino can be produced by reacting 4-(2,3,4,5,6-pentafluorophenoxy)piperidine 4a with an isocyanate or isothiocyanate of the formula R—N=C=O or R—N=C=S (wherein R is loweralkyl or aryl) at a temperature of from about 0° C. to about 50° C., preferably from about 20° C. to about 30° C., in a suitable solvent. Suitable solvents for this reaction include aromatic hydrocarbons such as, for example, benzene, xylene, toluene, and the like, benzene being preferred.

The reaction of the piperidine 4a with nitrourea provides a convenient means of effecting aminocarbonyl substitution. The reaction of 4-(2,3,4,5,6-pentafluorophenoxy)piperidine 4a with nitrourea is typically conducted at a temperature of from about 5° C. to about 100° C., preferably from about 50° C. to about 80° C., in a nonreactive organic solvent (e.g. alkanols such as ethanol, methanol, 1- and 2-propanol, 2-methoxyethanol, and the like; ethanol being preferred).

To provide 1-formyl-4-(2,3,4,5,6-pentafluorophenoxy)piperidine 5a, 4-(2,3,4,5,6-pentafluorophenoxy)piperidine 4a is reacted with formic acid and acetic anhydride at a temperature of from about 0° C. to about 50° C., preferably from about 20° C. to about 30° C. in a nonreactive organic solvent (e.g. ethereal solvents such as diethyl ether, tetrahydrofuran, 1,2-dimethoxyethane, bis(2-methoxyethyl) ether, and the like; diethyl ether being preferred).

The carbonylation of 4-(2,3,4,5,6-pentafluorophenoxy)piperidine 4a can also be accomplished by the reaction with a halide of the formula RC(O)Z or RC(S)Z (wherein R is loweralkyl, loweralkylamino, diloweralkylamino, arylamino, arylloweralkyl or heteroarylloweralkyl, and Z is halogen, preferably chlorine). This reaction is generally conducted at a temperature of from about 0° C. to about 50° C., preferably from about 10° C. to about 25° C. in the presence of a suitable base (e.g. alkali metal carbonates or bicarbonates, tertiary amines and the like, such as for example sodium carbonate, sodium bicarbonate, potassium bicarbonate, triethylamine, and the like). Halogenated hydrocarbons (e.g. dichloromethane, chloroform, carbon tetrachloride, and the like) are representative of suitable solvents for this reaction. Chloroform and dichloromethane are preferred.

Formula I compounds wherein R is a heteroarylloweralkyl are alternatively produced by reacting the piperidine 4a with, for example, chloroacetylchloride, and treating the resultant intermediate with the desired heteroaromatic compound (e.g., imidazole, pyrazole, indole, isoindole, and the like) to yield a 1-heteroaryl-loweralkylcarbonyl-4-(2,3,4,5,6-pentaflurophenoxy)-piperidine 5a. The reaction is generally conducted at a temperature of from about 0° C. to about 100° C., preferably from about 50° C. to about 80° C. in a dipolar aprotic solvent as previously described; dimethylformamide being preferred.

Included among the compounds of this invention are:
1-benzylcarbonyl-4-(2,3,4,5,6-pentafluorophenoxy)-piperidine;
4-(2,3,4,5,6-pentafluorophenoxy)-1-thioacetylpiperidine;
1-aminothiocarbonyl-4-(2,3,4,5,6-pentafluorophenoxy)piperidine;
1-(N,N-dimethylamino)thiocarbonyl-4-(2,3,4,5,6-pentafluorophenoxy)piperidine;
4-(2,3,4,5,6-pentafluorophenoxy)-1-[N-(4-trifluoromethylphenyl)-amino]carbonylpiperidine;

REACTION SCHEME

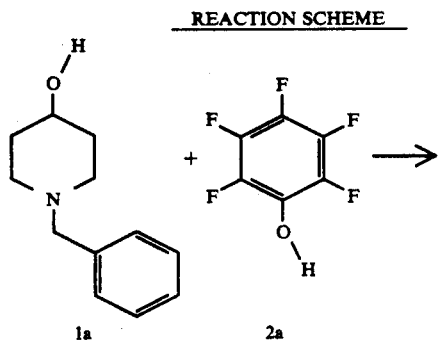

1a    2a

-continued
REACTION SCHEME

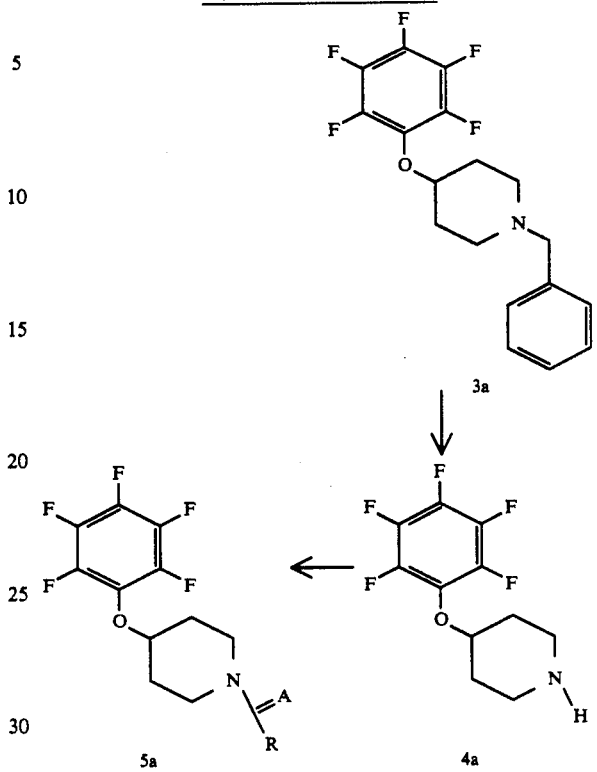

Wherein R is as herein defined
1-(N-phenylamino)carbonyl-4-(2,3,4,5,6-pentafluorophenoxy)piperidine;
1-[2-(imidazol-1-yl)thioacetyl]-4-(2,3,4,5,6-pentafluorophenoxy)piperidine;
4-(2,3,4,5,6-pentafluorophenoxy)-1-thioformylpiperidine; and
1-benzylthioacetyl-4-(2,3,4,5,6-pentafluorophenoxy)-piperidine.

The compounds of this invention are useful as anticonvulsants due to their anticonvulsant activity in mammals. Anticonvulsant activity is measured in male mice using the supramaximal electroshock (SES) assay described in Arch. Int. Pharmacodyn. 92, pp. 97–107, (1952) and the metrazol lethality assay (MTZ) described in J. Pharmacol. Exp. Ther., 81, 402 (1944).

Groups of male mice (Charles River, CD-1) weighing 18 to 30 g are employed in the SES assay. Test compounds are dissolved in distilled water, or if insoluble, suspended in water containing one drop of a surfactant, such as Tween-80. Test compounds are generally administered intraperitoneally at a dose of 10 ml of solution, or suspension, per kg of animal body weight. The output terminals of an A.C. shocker, which delivers 206 volts rms for 300 msec, are placed across the animals' eyes, an electrode paste coating assuring contact of the terminals with the eyes. The test compound is administered and thereafter the subject animals are shocked.

A test compound is considered to give protection if the mouse does not exhibit extensor tonus. Protection is expressed as normalized percent inhibition relative to vehicle control.

normalized % inhibition =

-continued $$\frac{\left[\frac{\# \text{ Rx Protected} - \# \text{ Control Protected}}{\# \text{ Rx Tested} - \# \text{ Control Tested}}\right]}{1 - \left[\frac{\# \text{ Control Protected}}{\# \text{ Control Tested}}\right]} \times 100$$

A time response is carried out using 6 animals per group. Animals are tested at 30, 60 and 120 minutes post drug. Additional time periods are tested if indicated by previous tests. A dose range determination is generally reserved for those compounds which inhibit convulsions by greater than about 45–55% at the screening dose employed at the time the test was performed. When the peak activity time has been determined, a dose response is initiated, using 10 animals per group at that time period.

Group of male mice (Charles River, CD-1), weighing 18 to 30 grams are employed in the Metrazol lethality assay. Test compounds are dissolved in distilled water or if insoluble, suspended in water, to which a surfactant, such as Tween-80 is added. The test compounds are administered orally, the administered dose being dissolved or suspended in 10 ml of solution or suspension per kg of animal body weight. Control animals (2 mice/group) receive water or water and Tween-80, i.e., the vehicle for administration of the test compound. Metrazol (pentylenetrazol) is dissolved in water (concentration 225 mg of Metrazol/10 ml of solution), and the solution is administered subcutaneously to groups of five animals each at one or more time intervals of 15, 30, 60, 90, or 120 minutes after administration of the test compound. The number of animal alive 15 minutes after treatment with Metrazol is determined and recorded. The following formula is employed to calculate the percent protection against Metrazol lethality.

$$\% \text{ protection} = \frac{\text{number of surviving mice}}{\text{number of treated mice}} \times 100$$

A dose range determination is performed by substantially the same procedure as the time response determination. In the dose range determination, five groups of 10 animals per group are employed. This determination is generally reserved for those compounds which protect against lethality by greater than 70% at the screening dose employed.

The anticonvulsant activity of several of the compounds of this invention as per the SES and MTZ assay procedures is provided in Table 1.

TABLE 1

| Compound | Anticonvulsant Activity | |
|---|---|---|
| | MTZ ED$_{50}$, mg/kg p.o. | SES ED$_{50}$, mg/kg i.p. |
| 1-(N-methylaminocarbonyl)-4-(2,3,4,5,6-pentafluorophenoxy)-piperidine | 35.9 | 62.5 |
| 1-(N,N-dimethylaminocarbonyl)-4-(2,3,4,5,6-pentafluorophenoxy)-piperidine | 40.4 | 50.2 |
| Phenobarbital | 16.9 | 8.4 |

Anticonvulsant activity is achieved when the compounds of this invention are administered to a subject requiring such treatment at an effective oral, parental or intravenous dose of from 10 to 100 mg/kg of body weight per day.

The compounds of this invention are also useful as antihypertensive agents due to their ability to depress blood pressure in mammals. Antihypertensive activity is measured in the spontaneous hypertensive rat by the indirect tail cuff method described in "Methods in Pharmacology", A. Schwartz, Ed., Vol. I, Appleton-Century Crofts, New York, N.Y., 1971, p. 135. In this procedure a group of five animals is treated orally for three days with the test compound in relation to a control group of the same number. The drop in blood pressure is measured on the third day following administration. The antihypertensive activities of representative compounds, expressed as a decrease in mean arterial blood pressure (in mm Hg), are given in Table 2 along with the activity of a standard compound.

TABLE 2

| SHR Compound | mm dec. in blood pressure at 50 mg/kg p.o. |
|---|---|
| 1-acetyl-4-(2,3,4,5,6-pentafluorophenoxy)piperidine | 36 |
| 1-aminocarbonyl-4-(2,3,4,5,6-pentafluorophenoxy)piperidine | 39 |
| Guanethidine | 20 |

Antihypertensive activity is achieved when the compounds of this invention are administered to a subject requiring such treatment at an effective oral, parental or intravenous dose of from 10 to 100 mg/kg of body weight per day.

The compounds of this invention are also useful as antidepressants by virtue of their ability to elicit an antidepressant response in mammals. Antidepressant activity is determined by the tetrabenazine induced ptosis assay in mice, [International Journal of Neuropharmacology, 8, 72 (1969], a standard assay for the determination of antidepressant activity.

In the tetrabenazine induced ptosis assay, male mice (Charles River, CD-1), weighing 20 to 39 g, are used in test groups of five animals. Test compounds are dissolved, or suspended with 1 drop of Tween-80, in distilled water and administered to the animals in volumes of 10 cc per kg of body weight. Tetrabenazine methanesulfonate (76.78% as the free base) is dissolved in distilled water and the concentration of the solution is adjusted so that the dose, administered intraperitoneally (i.p.) to the animals, is 40 mg of tetrabenazine base per kg of animal body weight.

The test compound is administered intraperitoneally (i.p.) or perorally (p.o.) to the subject animals, and the tetrabenazine solution is administered 30 minutes or 60 minutes, respectively, thereafter. Tetrabenazine solution and the solvent used to dissolve, or suspend, the test compounds are administered by the same route and at the same intervals as the test compounds to a control group.

The subject animals are placed in individual plastic containers (10 ½"×8"×6") thirty (i.p.) and sixty minutes (p.o.) after administration of the tetrabenazine solution, and one minute thereafter, the animals are scored for ptosis on the following scale:

| Eye Closure | Score |
|---|---|
| Eyes closed | 4 |
| Eyes ¾ closed | 3 |
| Eyes ½ closed | 2 |
| Eyes ¼ closed | 1 |

| Eye Closure | Score |
| --- | --- |
| Eyes open | 0 |

The total score for each group of 5 animals will therefore vary from 0 to 20; these scores are used as the indications of the activity of the test compound.

The vehicle-control group score is used as a determination of the validity of each test. The results are discarded and the test is repeated, if the control score is determined to be less than 17.

A dose range determination is generally reserved for those compounds which inhibit ptosis by greater than about 45–50% at the screening dose.

For calculation of the $ED_{50}$ value of a test compound; i.e., the calculated dose at which the test compound effects a 50% inhibition of tetrabenazine-induced ptosis, four or five doses are administered, and only vehicle-control scores of 17 to 20 are acceptable. A linear-regression analysis is used to estimate $ED_{50}$ values and 95% confidence limits.

The antidepressant activity of a representative compound is provided in Table 3.

TABLE 3

| Antidepressant Activity | |
| --- | --- |
| Compound | TBZ $ED_{50}$ mg/kg i.p. |
| 1-(N-methylaminocarbonyl)-4-(2,3,4,5,6-pentafluorophenoxy)-piperidine | 11.3 |
| Amitriptyline | 1.5 |

Antidepressant activity is achieved when the compounds of this invention are administered to a subject requiring such treatment at an effective oral, parental or intravenous dose of from 1 to 100 mg/kg of body weight per day.

It is to be understood that the dosages set forth above with respect to anticonvulsant, antidepressant, and antihypertensive activity for any particular subject should be adjusted according to the individual need and the professional judgment of the person administering or supervising the administration of the aforesaid compound. It is further understood that the dosages set forth herein are exemplary only and that they do not, to any extent, limit the scope or practice of the invention.

Effective amounts of the compounds of the present invention may be administered to a subject by any one of various methods, for example, orally as in capsules or tablets, parenterally in the form of sterile solutions or suspensions, and in some cases intravenously in the form of sterile solutions. The compounds of this invention, while effective themselves, may be formulated and administered in the form of their pharmaceutically acceptable acid addition salts for purposes of stability, convenience, increased solubility and the like.

Preferred pharmaceutically acceptable acid addition salts include salts of mineral acids, for example, hydrochloric acid, sulfuric acid, nitric acid and the like, salts of monobasic carboxylic acids such as, for example, carboxysuccinic acid, citric acid and the like.

Effective quantities of the compounds of this invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0 and 300 milligrams of the active compound.

The tablets, pills, capsules, troches and the like may also contain the following ingredients: a binder such as microcrystalline cellulose, gum tragancanth or gelatin; and excipient such as starch or lactose, a disintegrating agent such as alginic acid, Promogel ™, cornstarch and the like; a lubricant such as magnesium stearate or Sterotex; a glidant such as colloidal silicon dioxide; and a sweetening agent such as sucrose or saccharin or a flavoring agent such as peppermint, methyl salicylate, or orange flavoring. When the dosage unit is a capsule, it may contain, in addition to materials of the preceeding type, a liquid carrier such as a fatty oil. Other dosage unit forms may contain other various materials which modify the physical form of the dosage unit such as, for example, coatings. Thus, tablets or pills may be coated with sugar, shellac, or other enteric coating agents. A syrup may contain, in addition to the active compounds, sucrose and/or flavorings. Materials used in preparing these various compositions should be pharmaceutically pure and nontoxic in the amounts used.

For the purpose of parenteral therapeutic administration, the active compounds of this invention may be incorporated into a solution or suspension. These preparations should contain at least 0.1% of active compound, but may be varied between 0.5 and about 50% of the weight thereof. The amount of active compounds in such compositions is such that a suitable dosage will be obtained. Preferred compositions and preparations according to the present invention are prepared so that a parenteral dosage unit contains between 0.5 and 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose. The parenteral preparation can be enclosed in ampules, disposable syringes or multiple dose vials made of glass or plastic.

The following Examples are for illustrative purposes only and are not to be construed as limiting the invention.

EXAMPLES

Example 1

1-[(N-Methylamino)carbonyl]-4-(2,3,4,5,6-pentafluorophenoxy)piperidine

Step 1

A stirred mixture of 10.33 g of 1-benzyl-4-hydroxypiperidine, 9.93 g of pentafluorophenol, and 15.58 g of triphenylphosphine in 200 ml of benzene was cooled to 10° C. At this temperature, a solution of 10.35 g of diethyl azodicarboxylate in 50 ml of benzene was added, dropwise, over one hour. After stirring for 20 hours at ambient temperature, the reaction mixture was filtered and concentrated to an oil. The oil was purified by means of high pressure liquid chromatography (silica gel; elution with ethylacetate/dichloromethane 1:1). Evaporation of the appropriate fractions afforded 14.5 g of 1-benzyl-4-(2,3,4,5,6-pentafluorophenoxy)piperidine as an oil. Conversion of the free base to the corresponding hydrochloride salt afforded 8.2 g (42%) of 1-benzyl-4-(2,3,4,5,6-pentafluorophenoxy)piperidine hydrochloride, m.p. 244°–246° C.

ANALYSIS: Calculated for $C_{18}H_{16}F_5NO \cdot HCl$: 54.89% C 4.32% H 3.56% N Found: 55.33% C 4.57% H 3.54% N Step 2

To 2.0 g of 10% palladium on carbon was added 6.0 g of 1-benzyl-4-(2,3,4,5,6-pentafluorophenoxy)piperidine hydrochloride in 250 ml of methanol. The reaction mixture was pressurized to 50 psi with hydrogen and shaken on a Parr apparatus at room temperature for five hours. The mixture was then filtered and concentrated. Recrystallization of the concentrate from hot isopropanol afforded 1.9 g (42%) of 4-(2,3,4,5,6-pentafluorophenoxy)piperidine hydrochloride, m.p. 187°–190° C.

ANALYSIS: Calculated for $C_{11}H_{10}F_5NO \cdot HCl$: 43.49% C 3.62% H 4.61% N Found: 43.11% C 3.70% H 4.54% N Step 3

To a stirring solution of 5.3 g of 4-(2,3,4,5,6-pentafluorophenoxy)piperidine hydrochloride in 100 ml of benzene was added 2.37 ml of triethylamine followed by 1.00 ml of methyl isocyanate. The reaction mixture was stirred at ambient temperature for three hours and then evaporated to a semi-solid. The semi-solid was purified by means of high pressure liquid chromatography (silica gel; elution with 50% ethyl acetate/dichloromethane) to afford 5.14 g (93.3%) of 1-[(N-methylamino)carbonyl]-4-(2,3,4,5,6-pentafluorophenoxy)piperidine, m.p. 107°–110° C.

ANALYSIS: Calculated for $C_{13}H_{13}F_5N_2O_2$: 48.15% C 4.01% H 8.64% N Found: 47.15% C 3.97% H 8.55% N Example 2

1-[(N,N-Dimethylamino)carbonyl]-4-(2,3,4,5,6-pentafluorophenoxy)piperidine

To a stirring solution of 10 g of potassium carbonate in 50 ml of water was added 4.42 g of 4-(2,3,4,5,6-pentafluorophenoxy)piperidine hydrochloride in 50 ml of chloroform, followed by a solution of 3.23 g of dimethylcarbamoyl chloride in 20 ml of chloroform which was added, dropwise, over a period of 20 minutes. After stirring for 20 hours at room temperature, the layers were separated; the organic layer was washed with water followed by a saturated sodium chloride solution and dried over anhydrous magnesium sulfate. Filtration, followed by evaporation of the filtrate afforded an oil. The oil was purified by means of high pressure liquid chromatography (silica gel; elution with 5% methanol/dichloromethane) to afford 3.50 g (69.0%) of 1-[(N,N-dimethylamino)carbonyl]-4-(2,3,4,5,6-pentafluorophenoxy)piperidine as an oil.

ANALYSIS: Calculated for $C_{14}H_{15}F_5N_{22}$: 49.70% C 4.44% H 8.28% N Found: 49.25% C 4.63% H 8.14% N Example 3

1-[(N-Methylamino)thiocarbonyl]-4-(2,3,4,5,6-pentafluorophenoxy)piperidine

A stirring solution of 4.0 g of 4-(2,3,4,5,6-pentafluorophenoxy)piperidine in 50 ml of benzene was treated, dropwise, with a solution of 1.13 ml of methylisothiocyanate in 20 ml of benzene and then stirred at room temperature for three hours. Evaporation of the solvent under reduced pressure afforded an oil which was purified by means of high pressure liquid chromatography (silica gel; elution with 5% ethyl acetate/dichloromethane). Recrystallization of the resultant solid from isopropyl ether afforded 3.3 g (64%) of 1-[(N-methylamino)thicarbonyl]-4-(2,3,4,5,6-pentafluorophenoxy)piperidine, m.p. 97°–100° C.

ANALYSIS: Calculated for $C_{13}H_{13}F_5N_2OS$: 45.88% C 3.82% H 8.24% N Found: 45.81% C 3.78% H 8.30% N Example 4

1-[(2-Imidazol-1-yl)acetyl]-4-(2,3,4,5,6-pentafluorophenoxy)piperidine

Step 1

A chilled (ice bath temperature) solution of 10.0 g of 4-(2,3,4,5,6-pentafluorophenoxy)piperidine and 5.72 ml of triethylamine in 100 ml of dichloromethane was treated, dropwise, with a solution of 3.26 ml of chloroacetyl chloride in 40 ml of dichloromethane, and then stirred at room temperature for four hours. The reaction mixture was then washed with water followed by a saturated solution of sodium chloride, dried over anhydrous magnesium sulfate, filtered and concentrated to afford 13.35 g of 1-(2-chloroacetyl)-4-(2,3,4,5,6-pentafluorophenoxy)piperidine as an oil.

Step 2

A stirring solution of 7.11 g of imidazole in 100 ml of dimethylformamide was treated with a solution of 7.22 g of 1-(2-chloroacetyl)-4-(2,3,4,5,6-pentafluorophenoxy)piperidine in 50 ml of dimethylformamide and then stirred at 75° C. for five hours. After cooling, the reaction mixture was poured into water and extracted with ethyl acetate. The organic layer was washed with water followed by a saturated solution of sodium chloride, dried over anhydrous magnesium sulfate, filtered and concentrated to an oil. The oil was purified by means of high pressure liquid chromatography (silica gel; elution with 7.5% methanol/dichloromethane). Recrystallization of the resulting solid from ethyl acetate/hexane (10:1) afforded 3.70 g (47.0%) of 1-[(2-imidazol-1-yl)acetyl]-4-(2,3,4,5,6-pentafluorophenoxy)piperidine, m.p. 95°–96° C.

ANALYSIS: Calculated for $C_{16}H_{14}F_5N_3O_2$: 51.20% C 3.73% H 11.20% N Found: 50.91% C 3.78% H 11.14% N Example 5

1-Formyl-4-(2,3,4,5,6-pentafluorophenoxy)piperidine

A mixture of 1.5 ml of formic acid and 3.5 ml of acetic anydride was stirred at 55° C. for one hour, cooled, and treated with a solution of 4.0 g of 4-(2,3,4,5,6-pentafluorophenoxy)piperidine in 50 ml of diethyl ether. The reaction mixture was then stirred at ambient temperature for three hours. Thereafter, the mixture was poured into 100 ml of water, adjusted to pH 10 by the addition of sodium bicarbonate, and extracted with ethyl acetate. The organic layer was washed with water followed by a saturated solution of sodium chloride and dried over anhydrous magnesium sulfate. Filtration, followed by evaporation of the solvent afforded an oil which was purified by means of high pressure liquid chromatography (silica gel; elution with ethyl acetate) to yield 4.0 g (91%) of 1-formyl-4-(2,3,4,5,6-pentafluorophenoxy)piperidine, m.p. 32°-34° C.

ANALYSIS: Calculated for $C_{12}H_{10}F_5NO_2$: 48.82% C 3.41% H 4.75% N Found: 48.60% C 3.47% H 4.63% N

Example 6

1-Acetyl-4-(2,3,4,5,6-pentafluorophenoxy)piperidine

A stirring solution of 4.76 g of 4-pentafluorophenoxy)piperidine hydrochloride in 100 ml of dichloromethane was treated with 4.46 ml of triethyl amine followed by a solution of 1.413 g of acetyl chloride in 60 ml of dichloromethane (dropwise). After stirring at ambient temperature for 18 hours, the reaction mixture was washed with water followed by a saturated solution of sodium chloride and dried over anhydrous magnesium sulfate. Filtration, followed by evaporation of the solvents afforded an oil which was purified by means of high pressure liquid chromatography (silica gel; elution with 10% ethyl acetate/dichloromethane). The resultant oil solidified upon standing and this material was sublimed to 3.2 g (64.7%) of 1-acetyl-4-(2,3,4,5,6-pentafluorophenoxy)piperidine, m.p. 60°-65° C.

ANALYSIS: Calculated for $C_{13}H_{12}F_5NO_2$: 50.49% C 3.88% H 4.53% N Found: 50.44% C 3.93% H 4.58% N

Example 7

1-Aminocarbonyl-4-(2,3,4,5,6-pentafluorophenoxy)-piperidine

A solution of 4.0 g 4-(2,3,4,5,6-pentafluorophenoxy)-piperidine in 100 ml of 95% ethanol was treated with 1.73 g of nitrourea and then stirred at 65° C. for five hours. After cooling to room temperature, the reaction mixture was poured into water and extracted with ethyl acetate. The organic layer was washed with water followed by a saturated sodium chloride solution and dried over anhydrous magnesium sulfate. Filtration, followed by evaporation of the solvents afforded a residue which was purified by means of high pressure liquid chromatography (silica gel; elution with 5% methanol/dichloromethane). The resultant solid was recrystallized from hot isopropanol to yield 3.41 g (73.3%) of 1-aminocarbonyl-4-(2,3,4,5,6-pentafluorophenoxy)piperidine, m.p. 170°-172° C.

ANALYSIS: Calculated for $C_{12}H_{11}F_5N_2O_2$: 46.45% C 3.55% H 9.03% N Found: 46.34% C 3.56% H 8.97% N

What is claimed is:

1. A compound of the formula

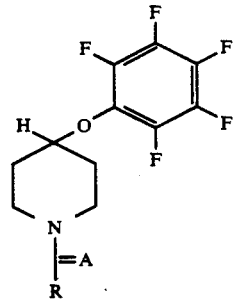

wherein A is oxygen or sulfur; and R is amino, loweralkylamino, diloweralkylamino or arylamino.

2. A compound as defined in claim 1 wherein A is oxygen.

3. The compound of claim 1 which is 1-[(N-methylamino)carbonyl]-4-(2,3,4,5,6-pentafluorophenoxy)piperidine.

4. The compound of claim 1 which is 1-[(N,N-dimethylamino)carbonyl]-4-(2,3,4,5,6-pentafluorophenoxy)-piperidine.

5. The compound of claim 1 which is 1-(aminocarbonyl)-4-(2,3,4,5,6-pentafluorophenoxy)piperidine.

6. A compound as defined in claim 1 wherein A is sulfur.

7. A compound as defined in claim 6 wherein R is amino, loweralkylamino, or diloweralkylamino or arylamino.

8. The compound of claim 7 which is 1-[(N-methylamino)thiocarbonyl]-4-(2,3,4,5,6-pentafluorophenoxy)piperidine.

9. A method of treatment which comprises administering to a mammal in need of relief from convulsions a pharmaceutically effective amount of a compound as defined in claim 1.

10. A method of treatment which comprises administering to a mammal in need of relief from depression a pharmaceutically effective amount of a compound as defined in claim 1.

11. An antihypertensive composition comprising an effective blood pressure lowering amount of the compound as defined in claim 1 and a pharmaceutically acceptable carrier therefor.

12. A method of treating a patient in need of relief from high blood pressure which comprises administering to the patient an effective amount of the compound as defined in claim 1.

13. A pharmaceutical composition for treating convulsions or treating depression which comprises a compound as defined in claim 1 present in an amount effective for treating convulsions or depression and a pharmaceutically acceptable carrier therefor.

* * * * *